United States Patent [19]

Sasaki et al.

[11] Patent Number: 5,024,093

[45] Date of Patent: Jun. 18, 1991

[54] FAN-SHAPE SCANNING ULTRASONIC FLAW DETECTING APPARATUS

[75] Inventors: Souji Sasaki; Hirotoshi Kino, both of Hitachi; Yoshinori Musha, Hitachiota; Jun Kubota; Hisao Okada, both of Hitachi, all of Japan

[73] Assignee: Hitachi, Ltd., Tokyo, Japan

[21] Appl. No.: 489,850

[22] Filed: Mar. 2, 1990

Related U.S. Application Data

[63] Continuation of Ser. No. 202,124, Jun. 3, 1988, abandoned.

[30] Foreign Application Priority Data

Jun. 5, 1987 [JP] Japan .................................. 62-139788
Nov. 11, 1987 [JP] Japan .................................. 62-283304

[51] Int. Cl.$^5$ .............................................. G01N 9/24
[52] U.S. Cl. ......................................... 73/633; 73/644
[58] Field of Search ................. 73/633, 628, 641, 620, 73/619, 618, 644; 128/661.01, 660.01, 662.03

[56] References Cited

U.S. PATENT DOCUMENTS

| | | | |
|---|---|---|---|
| 3,798,961 | 3/1974 | Flambard et al. | 73/644 |
| 3,978,712 | 9/1976 | Cowan et al. | 73/67.5 |
| 4,281,550 | 8/1981 | Erikson | 128/661.01 |
| 4,580,451 | 4/1986 | Miwa et al. | 73/626 |
| 4,622,517 | 11/1986 | Arnaud et al. | 73/633 |

FOREIGN PATENT DOCUMENTS

| | | | |
|---|---|---|---|
| 2429436 | 1/1980 | France . | |
| 2445545 | 7/1980 | France . | |
| 57-175252 | 10/1982 | Japan | 73/618 |
| 2016143 | 9/1979 | United Kingdom . | |

OTHER PUBLICATIONS

Proceedings of IEEE, vol. 67, No. 4, 1979, pp. 641-651, N.Y., U.S.A., M. G. Maginness, "Methods and Terminology for Diagnostic Ultrasound Imaging System", p. 643, Col. 1, line 61-644, col. 2, line 7; FIGS. 3-9.
Proceedings of IEEE, vol. 67, No. 4, 1979, 510-525, N.Y. 67, U.S.A.; G. S. Kino: "Acoustic Imaging for Nondestructive Evaluation": *Abstract; p. 516, Col. 2 line 8; FIG. 2a.
"Development of Electronic Sector Scanning Flaw Detector Turbine Blades"; by Y. Satou et al.
"Hitachi-Hyoron", vol. 64, No. 3, pp. 45-50, Mar., 1982.
"Electronic Sector Scanning for Ultrasonic Diagnosis", by J. C. Somers; Ultrasonics; Jul. 1968, pp. 153-159.

*Primary Examiner*—Hezron E. Williams
*Assistant Examiner*—Louis M. Arana
*Attorney, Agent, or Firm*—Kenyon & Kenyon

[57] ABSTRACT

A fan-shaped scanning flaw detecting apparatus which includes a probe provided with an ultrasonic wave transmitting-and-receiving array transducer arranged along a circular arc and an acoustic lens for converging and converting an ultrasonic beam transmitted/-received by the array transducer into a substantially parallel beam. The apparatus also includes a scanning function section that sequentially switches the transmitting and receiving operation of a group of operative transducer elements of the array transducer so as to make the ultrasonic beam perform fan-shaped scanning. A picturizing processor section forms a sectional image of an object to be examined on the basis of an echo signal obtained from the object to be examined and a display section displays the sectional image. A position detecting section detects a position where the ultrasonic beam is incident to the object to be examined when the probe is moved along a surface of the object to be examined. Image information of a sectional image of the object to be examined under a running path of the probe is formed by the picturizing processor section on the basis of two types of information, a first type representing the position of the ultrasonic beam incident to the object to be examined, which is obtained from the position detecting section, and a second type of information representing a position and relection intensity of the reflection source inside the object to be examined, which is obtained on the basis of a reflection signal of a transmitted ultrasonic pulse reflected by the reflection source. The sectional image information is then read and displayed by the display section.

3 Claims, 5 Drawing Sheets

FAN-SHAPE SCANNING ULTRASONIC FLAW DETECTING APPARATUS

This application is a continuation of application Ser. No. 202,124, filed June 3, 1988, now abandoned.

BACKGROUND OF THE INVENTION

The present invention generally relates to an ultrasonic flaw detecting apparatus, and particularly relates to a fan-shaped scanning flaw detecting apparatus in which scanning operation with a probe is smoothly achieved even upon a curved-surface of an object to be examined, while a superior ultrasonic transmission efficiency is maintained, and in which a focused ultrasonic beam is formed so that a superior azimuth resolution can be obtained.

In a conventional ultrasonic imaging apparatus for use for medical diagnosis or flaw detection by electronically performing fan-shaped scanning with a ultrasonic beam, as discussed in "Ultrasonics" (July, 1968, pp. 153 to 159), there has been employed a system in which the phase of the transmitting and receiving operation of transducer elements constituting a linear array transducer for transmitting and receiving ultrasonic waves is controlled to cause an ultrasonic beam to perform fan-shaped scanning within a required angular range so that an ultrasonic echo image inside a section of the fan-shape is displayed.

Alternatively, as disclosed in Hitachi-Hyoron, Vol. 64, No. 3, pp. 45-50, March 1982, there has been employed another system in which fan-shaped scanning with an ultrasonic beam is performed by sequentially shifting the transmitting and receiving operation of a series of transducer elements arranged on a circular arc in a linear array transducer for transmitting and receiving ultrasonic waves.

In the list of the these two systems in which the phase or delay time of the transmitting and receiving operation of the linear array transducer is controlled to deflect an ultrasonic beam to cause the ultrasonic beam to perform fan-shaped scanning, there have been disadvantages in the following points.

(1) There is a problem that an ultrasonic wave cannot be effectively transferred if an object to be examined has a curved or rough surface because it is necessary to cause at least the ultrasonic wave emitting-and-receiving surface of the linear array transducer to acoustically contact with the object to be examined.

(2) In order to improve the azimuth resolution, a system is employed in which the relative phase relationship between the respective transducer elements is adjusted to focus the ultrasonic beam at a predetermined position on an object to be examined. There is a problem that the effective portion is only within a limited focal range and there is low azimuth resolution in portions outside the focal range.

(3) Since it is necessary to accurately control the delay operation of the respective transducer elements in order to deflect the ultrasonic beam, it is necessary to provide a complicated and expensive function for adjusting a delay network.

In the second system in which an ultrasonic beam is deflected by the shifting operation of a circular-arc transducer array, there is a problem that it is necessary to adjust the phases of the respective operative elements in order to increase its azimuth resolution. The range of beam focusing is extremely limited in the same manner as the above item (2), and there is a further problem that it is necessary to provide a function for adjusting a delay network in the same manner as the above item (3).

SUMMARY OF THE INVENTION

It is therefore an object of the present invention to solve the foregoing problems in the prior art.

It is another object of the present invention to provide a fan-shaped scanning flaw detecting apparatus which has superior azimuth resolution over a wide range expanding in all directions, which has a superior ultrasonic transmission efficiency even if an object to be examined has a curved surface, and in which a circuit means for deflecting an ultrasonic beam at a high speed by electronic control is made simple and inexpensive.

In order to attain the foregoing objects, in an ultrasonic flaw detecting apparatus according to the present invention, a probe provided with an array transducer constituted by a plurality of ultrasonic transmitting-and-receiving transducer elements arranged on a circular arc is used, and a group of actuated or operative ones of the transducer elements are electronically switched and scanned so that the fan-shaped scanning with an ultrasonic beam is achieved without controlling the delay time. Moreover, the ultrasonic beam transmitted and received by the above-mentioned array transducer is focused at a point incident to an object to be examined so that the transmission of an ultrasonic wave can be sufficiently performed even if the contact surface between the object to be examined and the probe is extremely small in area. Further, in order to maintain superior azimuth resolution over a wide range of area to be examined and to obtain a precise flaw-detection image, an ultrasonic lens is provided in front of the array transducer so that the ultrasonic beam is made to penetrate in a focused and collimated state into the object to be examined.

DETAILED DESCRIPTION

Figure 1:
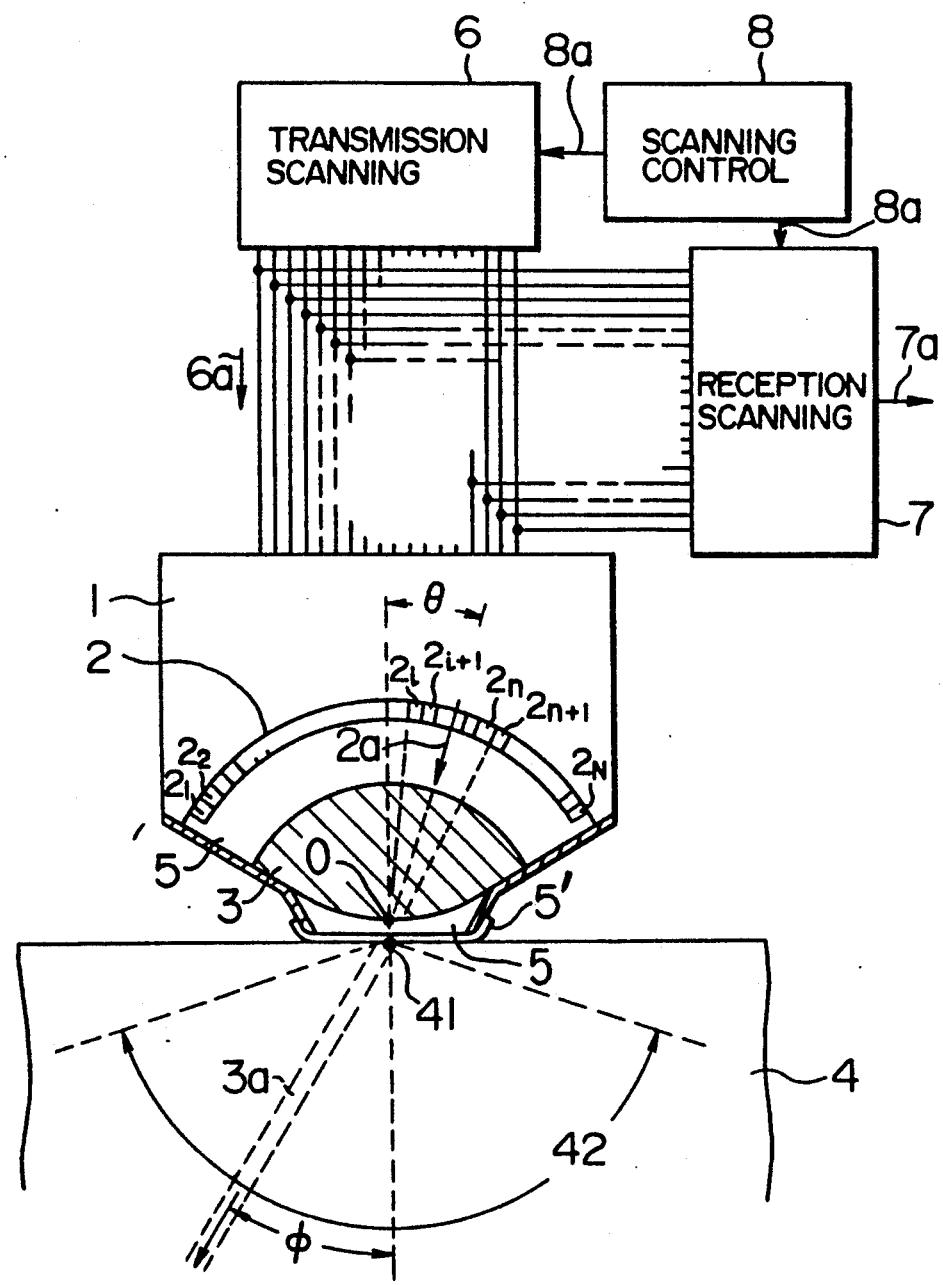
FIG. 1 is a diagram illustrating an arrangement of an embodiment of a probe section of a flaw detecting apparatus according to the present invention.

Referring to FIG. 1, the arrangement and operation of a probe section which is a main part of the fan-shaped scanning flaw detecting apparatus according to the present invention will be described hereunder. A probe 1 for transmitting and receiving an ultrasonic wave is provided with an array transducer 2 constituted by a number of transducer elements $2_1, \ldots, 2_N$ arranged on a circular arc. A group of operative transducer elements $2_i, \ldots, 2_n$ of the array transducer 2 are caused to simultaneously perform operations of transmitting and receiving an ultrasonic wave so that the probe 1 can transmit or receive a focused ultrasonic beam $2a$. An ultrasonic collimator lens 3 having a diverging function to convert a converging ultrasonic beam into a parallel beam is provided in front of the array transducer 2 so that the ultrasonic beam 2a is converted into a collimated beam 3a by the collimator lens 3 and the collimated beam 3a is made to penetrate into an object 4 to be examined.

Assuming now that switching is made in such a manner that among the transducer elements $2_l, \ldots, 2_N$ of the array transducer 2, a group of elements to be operative or actuated are sequentially shifted, for example, from a group of elements $2i, \ldots, 2n$, into another group of elements $2_{i+1}, \ldots, 2_{n+1}$, and then to still another group of elements $2_{i+2}, \ldots, 2_{n+2}, \ldots$ Accordingly, a transmitting-and-receiving angle $\theta$ of the ultrasonic beam 2a is sequentially changed and therefore an incident angle $\phi$ of the beam 3a incident into the object 4 to be examined is sequentially changed so as to achieve the fan-shape scanning in the object 4 to be examined by means of an ultrasonic beam.

The apparatus according to the present invention has a significant feature in that since the ultrasonic beam 2a is converted into the parallel beam 3a by the collimator lens 3 after the ultrasonic beam 2a has been converged once, superior azimuth resolution can be obtained in detecting a reflection source in the object 4 to be examined, and since the energy diffusion of the beam 3a is small even after the beam 3a is propagated over a long path, high examination sensitivity can be obtained even for a long distance.

An ultrasonic wave transmitting medium 5 is interposed among the array transducer 2, the collimator lens 3 and the object 4 to be examined, the medium 5, which may be a liquid medium, being maintained by a film 5'of a flexible natural. The medium 5 is selected so that the sonic velocity in the medium 5 is lower than that in the collimator lens 3. The collimator lens 3 is shaped to be a convex lens so as to be able to convert the converging beam 2a into the parallel beam 3a. By using the probe 1 arranged in such a manner as described above, an extremely narrow range is sufficient for a boundary portion 41 in which the ultrasonic beam 2a is incident to the object 4 to be examined, so that it becomes easy to maintain the acoustic contact between the probe 1 and the object 4 to be examined. Moreover, since the scanning by the ultrasonic beam 3a is performed over an extensive area inside the object 4 to be examined, the apparatus is suitable for the examination of an extensive area. The above-mentioned transmitting and receiving operation of the array transducer 2 is achieved by the operation of a transmission scanning 6 and a reception scanning section 7 under control of a scanning control section 8. The control operation will be described hereunder with reference to FIG. 2.

Figure 2:
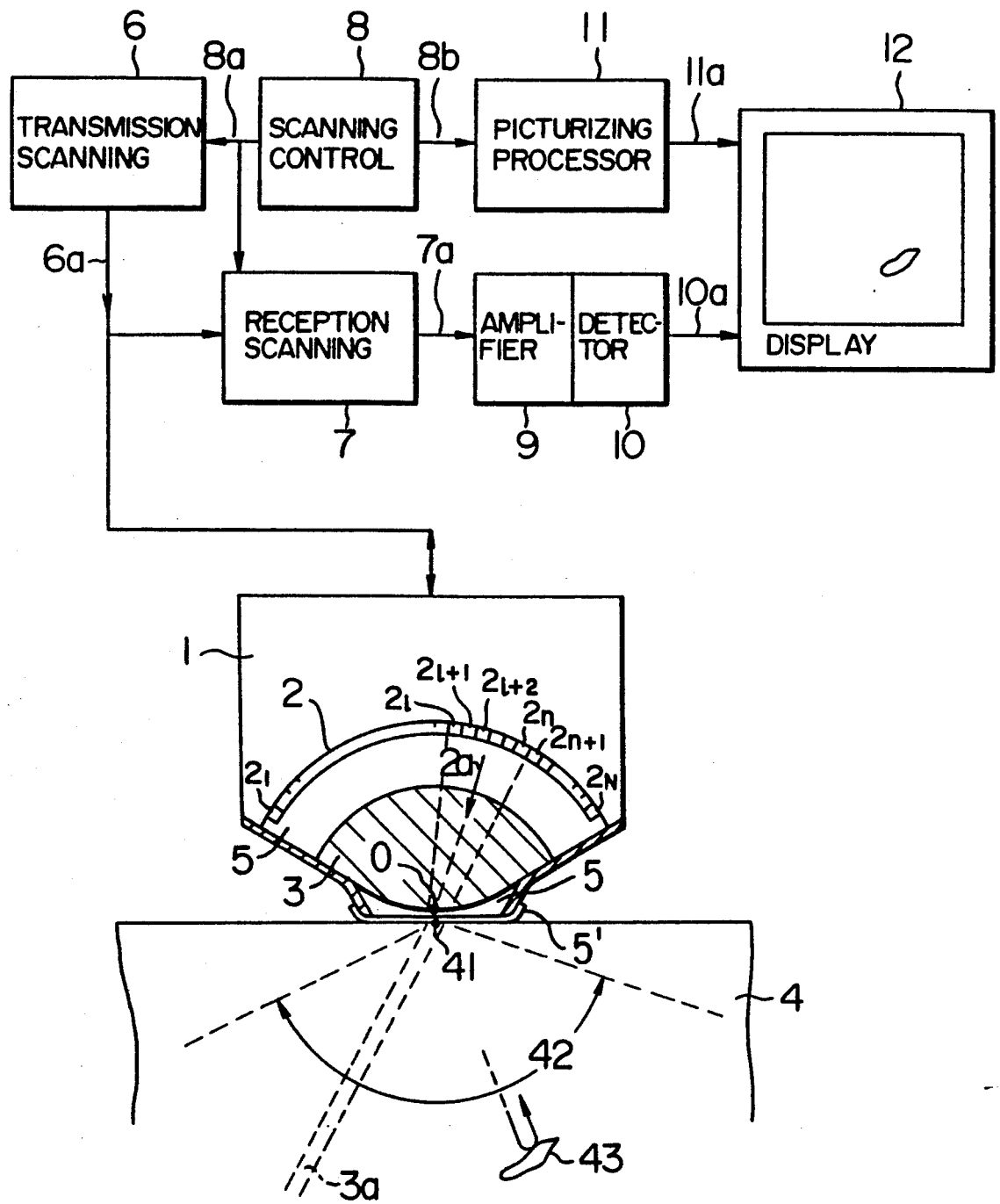
FIG. 2 is a block diagram illustrating a whole arrangement with the probe section of FIG. 1 as a main component.

FIG. 2 is a diagram illustrating a specific arrangement of the apparatus according to the present invention, and the operation of each portions thereof will be described.

The transmission scanning section 6 is arranged to selectively excite, for example, a group of operative transducer elements $2_i, \ldots, 2_n$ among the transducer elements $2_l, \ldots, 2_N$ of the array transducer 2 by its output transducer exciting signal 6a so as to cause the selectively excited group of operative transducer elements to perform the ultrasonic wave transmitting operation. The transmission scanning section 6 has a function to sequentially shift the group of transducer elements to which the transducer exciting signal 6a is to be applied, for example, from the group of operative transducer elements $2_i, \ldots, 2_n$, into another group of transducer elements $2_{i+1}, \ldots, 2_{n+1}$, and to still another group of transducer elements $2_{i+2}, \ldots, 2_{n+2}, \ldots$ so that shift scanning is performed. By such transmission scanning, the ultrasonic beam 3a incident to the object 4 to be examined through the lens 3 performs scanning a fan-shaped area substantially centering the beam incident point 41 on the object 4 to be examined so as to establish the condition for obtaining a reflected wave from an acoustic boundary having a variety of directional properties of reflection and existing inside the object 4 to be examined.

The ultrasonic wave reflected on an acoustic boundary such as a flaw or the like inside the object 4 to be examined arrives again at the group of transducer elements which transmitted the beam 3a, for example, the group of transducer elements $2_i, \ldots, 2_n$. The receiving operation is sequentially shifted from the group of transducer elements $2_i, \ldots, 2_n$ into the group of transducer elements $2_{i+1}, \ldots, 2_{n+1}$, and then to the group of the transducer elements $2_{i+2}, \ldots, 2_{n+2}, \ldots$, in a manner similar to the case of the above-mentioned transmitting operation so that the reception scanning is performed. As the result, the transmitting and receiving operation of the ultrasonic beam 3a for fan-shaped scanning over the area 42 substantially centering the incident point 41 of the beam 3a is achieved by the transmission scanning section 6 and the reception and scanning section 7.

The scanning controlling section 8 is arranged to generate a control signal 8a used by the transmission scanning section 6 and the reception scanning section 7 for performing the above-mentioned operation to shift the group of transducer elements of the array transducer 2 for transmitting and receiving an ultrasonic wave. By use of the thus arranged operating mechanism, the ultrasonic beam transmitted and received by the probe 1 having a circular-arcuate array transducer 2 scans an area in a section of the object 4 to be examined, and an echo signal 7a obtained from various directions is sent out as a video signal 10a through a signal amplifier section 9 and a signal detector section 10.

A picturizing processor section 11 is arranged to obtain the position of an echo source for example such as represented by 43 on the basis of the video signal 10a from the detector section 10 and an output signal 8b of the scanning control section 8 representing information about the direction of the ultrasonic beam 3a obtained by the scanning controlling section 8. The picturizing processor section 11 addresses the video signal 10a to the obtained position to thereby produce an image signal 11a for forming a sectional image of the fan-shape scanned area of the object 4 to be examined.

A display section 12 displays the above-mentioned sectional image on the basis of the image signal 11a from the picturizing processor section 11 in the same manner as in a conventional ultrasonic imaging apparatus.

Figure 3:
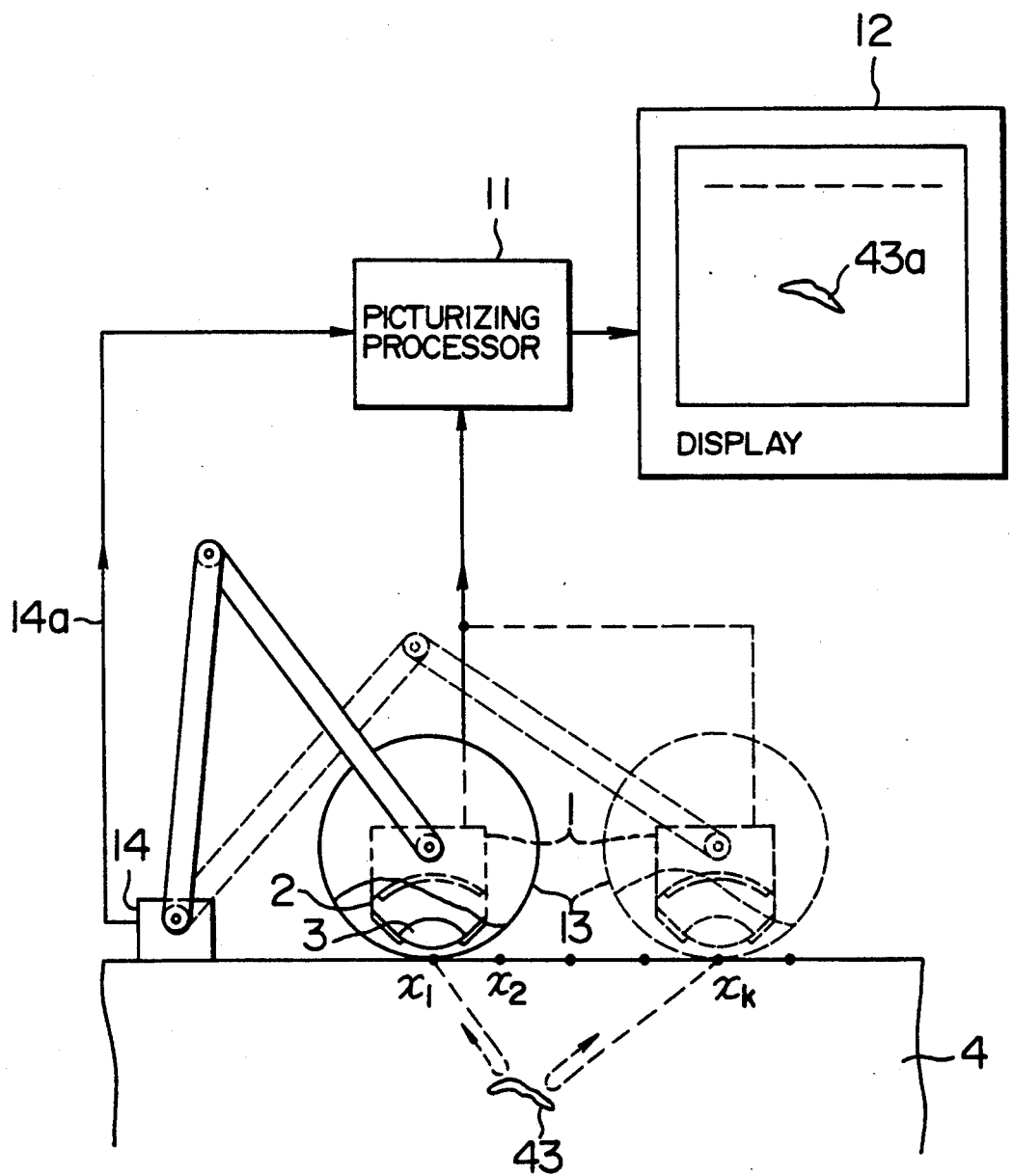
FIG. 3 is a diagram illustrating an example of application of the present invention.

An example of an application of the present invention will be described with reference to FIG. 3.

A probe 1 used in this application is provided with an array transducer 2 arranged along a circular arc, an ultrasonic collimator lens 3 and an ultrasonic wave transmitting medium 5 accommodated in a tire 13. A position x of the probe 1 on a surface of an object 4 to be examined is detected by a detector 14 which produces an output signal 14a representing information as to the detected position x, the output signal 14a being in turn led to a picturizing processor section 11. The echo images obtained at various positions $x_l, \ldots, x_k$ of the probe 1 are superimposed one on the other in the picturizing processor section 11 so that an image of signals from a reflection source 43 having a variety of directional properties of reflection is obtained on a display section 12 as an image 43a showing the real shape of the reflection source 43. Thus, the real shape of a reflection source can be well expressed even if the shape of the reflection source is relatively complicated.

Figure 4:
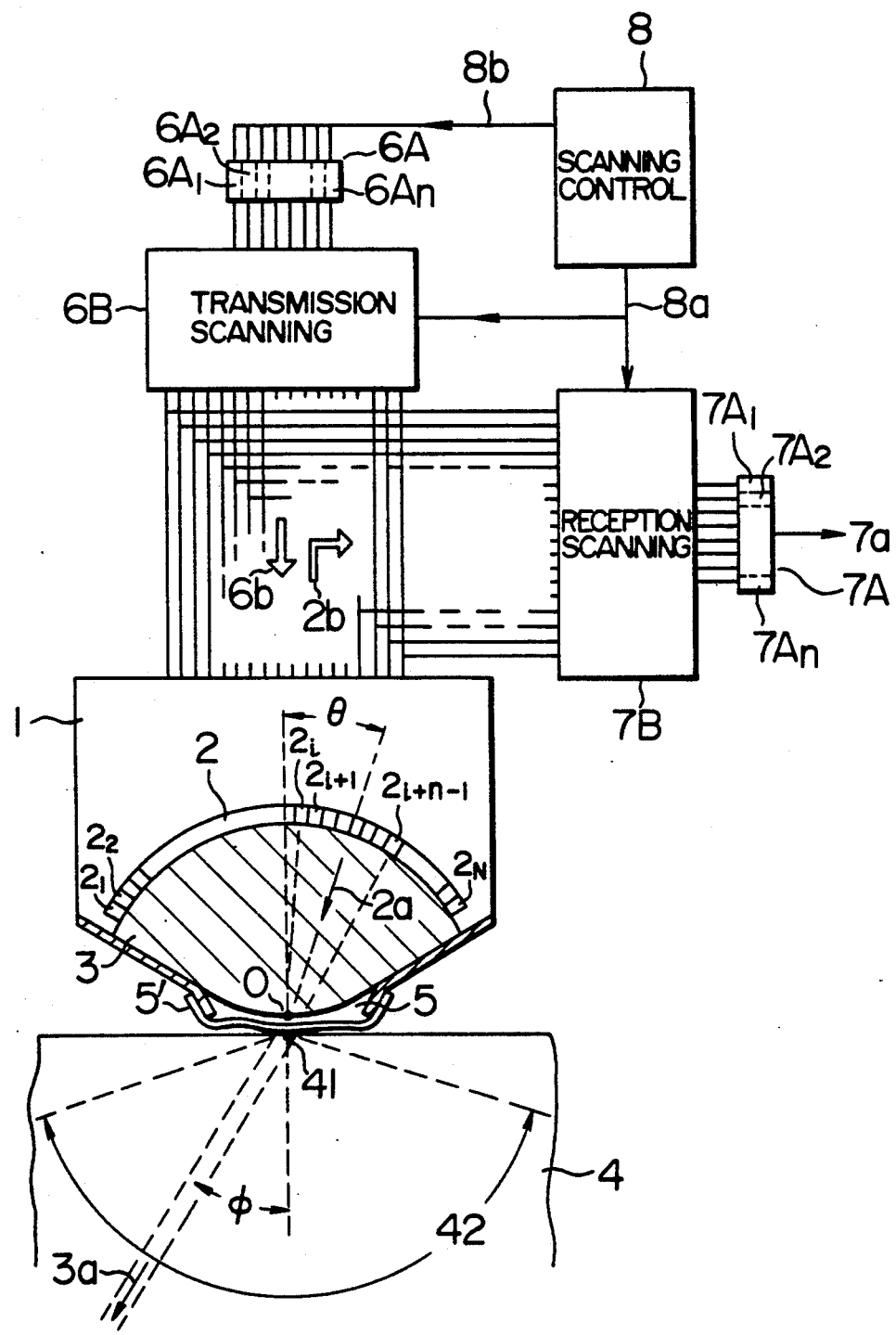
FIG. 4 is a diagram illustrating an arrangement of a second embodiment of the probe section of the flaw detecting apparatus according to the present invention.

FIG. 4 illustrates a second embodiment in which a delay line circuit is used in order to further improve the beam control function by an acoustic lens. In the embodiment of FIG. 4, the construction is fundamentally the same as that of the embodiment in FIG. 1 and therefore the description of the same portions is omitted, and the parts the same as or equivalent to those in FIG. 1 are referenced correspondingly.

In FIG. 4, in the transmitting and receiving operation of a group of operative transducer elements, for example, n transducer elements $2_i, 2_{i+1}, \ldots, 2_{i+n-1}$ are made to perform a transmitting operation 2b in response to a transmission signal 6b which is produced from a transmission scanning section 6B in response to a transmission command signal 8b which is applied to the transmission scanning section 6B from a scanning control section 8 through a delay line circuit 6A constituted by delay lines $6A_1, 6A_2, \ldots, 6A_n$. Signals received by the above-mentioned transducer elements are passed through a reception scanning section 7B and a delay line circuit 7A constituted by delay lines $7A_1, 7A_2, \ldots, 7A_n$ so as to be matched to be in phase into a reception signal 7a. Consequently, when the ultrasonic beam 2a passes the center O of the circular-arcuate array of the transducer, the beam 2a is somewhat widened so that the beam control function by the lens 3 is improved.

Figure 5:
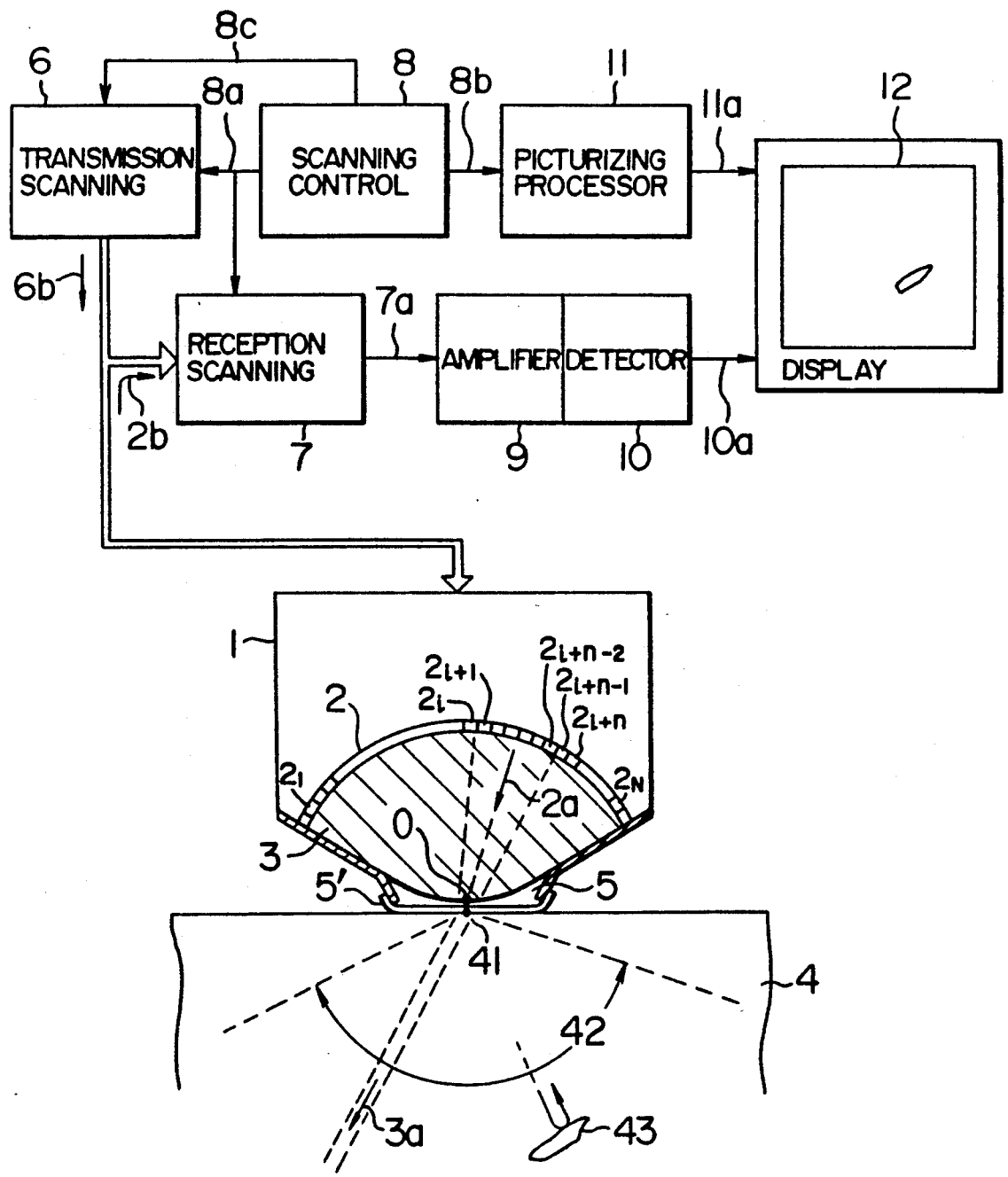
FIG. 5 is a block diagram illustrating a whole arrangement with the probe section of FIG. 4 as a main component.

FIG. 5 is a block diagram illustrating the whole arrangement of the embodiment of FIG. 4, which is fundamentally the same as that shown in FIG. 2. Only the parts different from those shown in FIG. 2 will be described.

In FIG. 5, a scanning control section 8 is arranged to generate a transmission command signal 8c and a control signal 8a which is used by a transmission scanning section 6 and a reception scanning section 7 for shifting the operative transducer elements of the array transducer 2 which transmits and receives an ultrasonic wave in such a manner as described above. By use of the thus arranged operating mechanism, the ultrasonic beam transmitted and received by the probe 1 having a circular-arcuate array transducer 2 scans an area in section of the object 4 to be examined, and an echo signal 7a obtained from various directions is sent out as a video signal 10a through a signal amplifier section 9 and a signal detector section 10.

According to the above-mentioned fan-shaped scanning flaw detecting apparatus of the present invention, since an extremely converged and collimated ultrasonic beam scans the inside of an object to be examined in a fan-shaped area so that an image of an acoustic boundary inside of the object to be examined formed by an echo signal is displayed, the displayed image is superior in azimuth resolution is precise, and extremely close to the actual shape of the flaw. The apparatus therefore has such an effect that, for example, when a flaw inside a material is examined, it is easy to immediately estimate the size and shape of the flaw.

The apparatus according to the present invention has such a further effect that since an ultrasonic wave sufficiently converged is incident into an object to be examined and the substantial center of the examined fan-shaped area corresponds to the incident point of the ultrasonic wave so that the ultrasonic wave is transmitted from the extremely limited portion of a probe to the object to be examined. The ultrasonic wave is efficiently transmitted even if the object to be examined has a curved or rough surface.

In order to realize an effect to converge an ultrasonic beam over the whole path of the beam, conventionally, a system in which a focal area of the beam is formed by controlling the phase of a group of operative transducer elements and the position of the focal area is sequentially shifted so that the examined pieces of information obtained within the focal areas are joined to each other. In the case of employing such a system, there have been disadvantages in that not only a complicated delay line network and a control section for controlling the switching of the operation of the delay line network are required so that the apparatus becomes expensive, but also the time required for forming an examined image is prolonged.

In the apparatus according to the present invention, on the contrary, such a delay line network for forming a focal area and such a controlling section therefor as described above become unnecessary, so that not only the cost can be reduced but the time required for forming an examined image can be shortened by the extreme simplification of the apparatus.

Through the above-mentioned superior effects, the apparatus according to the present invention will bring a great advantage into the industrial field.

What is claimed is:

1. In a fan-shaped scanning flaw detecting apparatus comprising:

a probe provided with an ultrasonic wave transmitting-and-receiving array transducer arranged along a circular arc and an acoustic lens diverging and converting an ultrasonic beam transmitted/received by said array transducer into a substantially parallel beam, said array transducer having a circular arc; and a scanning function section sequentially switching the transmitting and receiving operation of a group of operative transducer elements of said array transducer so as to make said ultrasonic beam perform fan-shaped scanning, whereby an echo signal from an object to be examined is obtained by the transmitting and receiving operation of said group of operative transducer elements so as to detect a flaw in the object, the improvement comprising:

a flexible material that provides a contact point to an object to be examined;

said acoustic lens being unitary and having a top portion, said top portion of said acoustic lens being convex and being positioned at a center of the circular arc of said array transducer, said acoustic lens being positioned between said array transducer and said flexible material, a surface of said acoustic lens on the side of said array transducer having a shape substantially the same as said circular arc of said array transducer; and an ultrasonic wave transmitting fluid disposed between said top portion of said acoustic lens and said flexible material, said fluid having an ultrasonic wave velocity less than that of said acoustic lens.

2. The fan-shaped scanning flaw detecting apparatus according to claim 1, in which the group of operative transducer elements of said array transducer are respectively connected to corresponding delay lines so as to make controllable a focal point of said ultrasonic beam convergently transmitted/received to/from a center of said circular arc by said group of operative transducer elements.

3. The fan-shaped scanning flaw detecting apparatus of claim 1, further comprising:

a picturizing processor section for forming a sectional image of the object to be examined on the basis of an echo signal obtained from said object to be examined; and a display section for displaying said sectional image.

* * * * *

UNITED STATES PATENT AND TRADEMARK OFFICE
CERTIFICATE OF CORRECTION

PATENT NO.  : 5,024,093
DATED       : 18 June 1991
INVENTOR(S) : Souji SASAKI et al.

It is certified that error appears in the above-identified patent and that said Letters Patent is hereby corrected as shown below:

<u>Column</u>  <u>Line</u>

3      34      Change "natural" to --material--.
5      60      After "resolution" insert --,--.

Signed and Sealed this

Twelfth Day of January, 1993

Attest:

DOUGLAS B. COMER

*Attesting Officer*     Acting Commissioner of Patents and Trademarks